(12) United States Patent
Stark et al.

(10) Patent No.: US 9,167,822 B2
(45) Date of Patent: Oct. 27, 2015

(54) ANTIFUNGAL COMPOSITIONS

(75) Inventors: Jacobus Stark, Echt (NL); Angelique De Rijk, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/985,371

(22) PCT Filed: Mar. 1, 2012

(86) PCT No.: PCT/EP2012/053518

§ 371 (c)(1),
(2), (4) Date: Aug. 14, 2013

(87) PCT Pub. No.: WO2012/117060

PCT Pub. Date: Sep. 7, 2012

(65) Prior Publication Data

US 2013/0324488 A1    Dec. 5, 2013

(51) Int. Cl.
| | |
|---|---|
| *A61K 31/70* | (2006.01) |
| *A01N 43/90* | (2006.01) |
| *A01N 43/56* | (2006.01) |
| *A01N 47/18* | (2006.01) |
| *A23L 3/3463* | (2006.01) |

(52) U.S. Cl.
CPC ............. *A01N 43/90* (2013.01); *A01N 43/56* (2013.01); *A01N 47/18* (2013.01); *A23L 3/34635* (2013.01)

(58) Field of Classification Search
CPC ........ A01N 43/90; A01N 43/56; A01N 47/18
USPC .............................................. 514/31
See application file for complete search history.

(56) References Cited

U.S. PATENT DOCUMENTS

| | | |
|---|---|---|
| 5,597,598 A | 1/1997 | van Rijn et al. |
| 7,329,633 B2 * | 2/2008 | Dunkel et al. ............... 504/280 |
| 2008/0234210 A1 * | 9/2008 | Rijn et al. ..................... 514/28 |

FOREIGN PATENT DOCUMENTS

| | | |
|---|---|---|
| EP | 2071953 A1 | 6/2009 |
| WO | 2010091803 A2 | 8/2010 |
| WO | 2011056291 A1 | 5/2011 |

OTHER PUBLICATIONS

International Search Report for PCT/EP2012/05318 Mailed May 14, 2012.

* cited by examiner

*Primary Examiner* — Elli Peselev
(74) *Attorney, Agent, or Firm* — Miles & Stockbridge P.C.

(57) ABSTRACT

The present invention relates to new antifungal compositions and their use in the treatment of agricultural products.

12 Claims, No Drawings

ANTIFUNGAL COMPOSITIONS

CROSS REFERENCE TO RELATED APPLICATIONS

This application is a §371 National Stage Application of PCT/EP2012/053518, filed Mar. 1, 2012, which claims priority to European Application No. 11156788.9, filed Mar. 3, 2011.

BACKGROUND OF THE INVENTION

1. Field of the Invention

FIELD OF THE INVENTION

The present invention discloses new antimicrobial compositions to control plant diseases and to prevent microbial spoilage of crops.

2. Description of Related Art

It is estimated that about 25% of the world crop production is lost due to microbial spoilage, of which spoilage by fungi is by far the most important cause. Not only from an economical point of view, but also from a humane point of view it is of great importance to prevent spoilage of food products. After all, in many parts of the world people suffer from hunger.

Success in combating plant and crop diseases and in reducing the damage they cause to yields and quality depends greatly on the timely application of fungicides. The prolonged and frequent use of many fungicides such as e.g. benzamidazoles has contributed to reduce their effectiveness thanks to the development of phenomena of resistance.

An important class of fungicides are the pyrazoles. Pyrazole fungicides have attracted attention from many industrial companies. This led to the commercial introduction of for instance furametpyr, used to control rice sheat blight, and penthiopyrad having activity against gray mold, powdery mildew, apple scab, rusts, *Rhizoctonia* and *Botrytis* (see e.g. Vicentini et al. 2007). In WO 2010/091803 the use of succinate dehydrogenase inhibitors such as penthiopyrad, fluopyram, bixafen and isopyrazam, for extending shelf life and storage stability of fruits and vegetables is disclosed. Despite their current sensitivity to pyrazole fungicides, there is a high risk that many fungi will acquire resistance against against these fungicides in time.

For many decades, the polyene macrolide antimycotic natamycin has been used to prevent fungal growth on food products such as cheeses and sausages. This natural preservative, which is produced by fermentation using *Streptomyces natalensis*, is widely used throughout the world as a food preservative and has a long history of safe use in the food industry. In U.S. Pat. No. 5,597,598 the use of an antifungal composition comprising a polyene antifungal compound, an acidic antifungal compound and an additional organic acid or its alkali or earth alkali salt to treat food and agricultural products is disclosed. Natamycin is very effective against all known food spoilage fungi. Although natamycin has been applied in e.g. the cheese industry for many years, up to now development of resistant fungal species has never been observed.

Consequently, it can be concluded that there is a severe need for more effective, more environmental friendly, lower-toxicity and less harmful antimicrobial compositions, e.g. antifungal compositions, for the treatment of fungal growth in and on plants and crops.

SUMMARY

The present invention solves the problem by providing a new synergistic antimicrobial, e.g. antifungal, composition comprising a polyene antifungal compound and at least one antifungal compound from the family of pyrazole fungicides. As used herein, the term "synergistic" means that the combined effect of the antifungal compounds when used in combination is greater than their additive effects when used individually.

DETAILED DESCRIPTION OF A PREFERRED EMBODIMENT

In general, synergistic activity of two active ingredients can be tested in for example the analysis of variance model using the treatment interaction stratum (see Slinker, 1998). Relative efficacy can be calculated by means of the following formula: ((value of evolution status of untreated control−value of evolution status of composition)/(value of evolution status of untreated control))*100. An interaction coefficient can then be calculated by means of the following formula: ((relative efficacy of combination compound A+compound B)/(relative efficacy of compound A+relative efficacy of compound B))*100. An interaction coefficient larger than 100 indicates synergy between the compounds.

Alternatively, synergy can be calculated as follows: the antifungal activity (in %) of the individual active ingredients can be determined by calculating the reduction in mould growth observed on products treated with the active ingredients in comparison to the mould growth on products treated with a control composition. The expected antifungal activity (E in %) of the combined antifungal composition comprising both active ingredients can be calculated according to the Colby equation (Colby, 1967): $E=X+Y-[(X \cdot Y)/100]$, wherein X and Y are the observed antifungal activities (in %) of the individual active ingredients X and Y, respectively. If the observed antifungal activity (O in %) of the combination exceeds the expected antifungal activity (E in %) of the combination and the synergy factor O/E is thus >1.0, the combined application of the active ingredients leads to a synergistic antifungal effect.

In an embodiment of the invention, the at least one antifungal compound from the family of pyrazole fungicides is selected from the group consisting of bixafen, fenpyrazamine, fluxapyroxad, furametpyr, isopyrazam, penflufen, penthiopyrad, rabenzazole and sedaxane. In an embodiment the compositions may also contain two or more different antifungal compounds from the family of pyrazole fungicides. It is to be understood that derivatives of antifungal compounds from the family of pyrazole fungicides including, but not limited to, salts or solvates of antifungal compounds from the family of pyrazole fungicides or modified forms of antifungal compounds from the family of pyrazole fungicides may also be applied in the compositions of the invention. Examples of commercial products containing pyrazole fungicides such as bixafen are the products with the brand name Aviator® 235 Xpro™ and Siltra® Xpro™. Said commercial products can be incorporated in the present invention.

In an embodiment the polyene antifungal compound is selected from the group consisting of natamycin, nystatin, amphotericin B, trienin, etruscomycin, filipin, chainin, dermostatin, lymphosarcin, candicidin, aureofungin A, aureofungin B, hamycin A, hamycin B and lucensomycin. In a preferred embodiment the polyene antifungal compound is natamycin. In an embodiment the compositions may also contain two or more different polyene antifungal compounds. It is to be understood that derivatives of polyene antifungal compounds including, but not limited to, salts or solvates of polyene antifungal compounds or modified forms of polyene antifungal compounds may also be applied in the compositions of the invention. Examples of commercial products containing natamycin are the products with the brand name Delvocid®. Such products are produced by DSM Food Specialties (The Netherlands) and may be solids containing e.g. 50% (w/w) natamycin or liquids comprising between e.g. 2-50% (w/v) natamycin. Said commercial products can be incorporated in the compositions of the invention.

The composition of the present invention generally comprises from about 0.005 g/l to about 100 g/l and preferably from about 0.01 g/l to about 50 g/l of a polyene antifungal compound. Preferably, the amount is from 0.01 g/l to 3 g/l.

The composition of the present invention generally comprises from about 0.0001 g/l to about 2000 g/l and preferably from about 0.0005 g/l to about 1500 g/l of an antifungal compound from the family of pyrazole fungicides. More preferably, the amount is from 0.001 g/l to 1000 g/l.

In an embodiment the composition of the present invention further comprises at least one additional compound selected from the group consisting of a sticking agent, a carrier, a colouring agent, a protective colloid, an adhesive, a herbicide, a fertilizer, a thickening agent, a sequestering agent, a thixotropic agent, a surfactant, a further antimicrobial compound, a detergent, a preservative, a spreading agent, a filler, a spray oil, a flow additive, a mineral substance, a solvent, a dispersant, an emulsifier, a wetting agent, a stabiliser, an antifoaming agent, a buffering agent, an UV-absorber and an antioxidant. A further antimicrobial antifungal compound may be an antifungal compound (e.g. imazalil, thiabendazole or chlorthalonil) or a compound to combat insects, nematodes, mites and/or bacteria. Of course, the compositions according to the invention may also comprise two or more of any of the above additional compounds. Any of the above mentioned additional compounds may also be combined with the polyene antifungal compound and/or the at least one antifungal compound from the family of pyrazole fungicides in case the antifungal compounds are applied separately. In an embodiment the additional compounds are additives acceptable for the specific use, e.g. food, feed, medicine, cosmetics or agriculture. Additional compounds suitable for use in food, feed, medicine, cosmetics or agriculture are known to the person skilled in the art.

In a specific embodiment the further antimicrobial compound is a natural crop protection compound belonging to the group of phosphites, e.g. $KH_2PO_3$ or $K_2HPO_3$ or a mixture of both phosphite salts. Phosphite containing compounds as used herein means compounds comprising a phosphite group, i.e. $PO_3$ (in the form of e.g. $H_2PO_3^-$, $HPO_3^{2-}$ or $PO_3^{3-}$) or any compound which allows the release of a phosphite ion including compounds such as phosphorous acid and phosphonic acid as well as derivatives thereof such as esters and/or alkali metal or alkaline earth metal salts thereof. In case the compositions of the present invention comprise a polyene antifungal compound (e.g. natamycin) and at least one phosphite containing compound, they preferably comprise 0.1 g or less lignosulphonate, more preferably 0.1 g or less polyphenol, per gram polyene antifungal compound. Preferably, they comprise 0.01 g or less lignosulphonate, more preferably 0.01 g or less polyphenol, per gram polyene antifungal compound. In particular, they are free of lignosulphonate and preferably free of polyphenol. Suitable examples of phosphite containing compounds are phosphorous acid and its (alkali metal or alkaline earth metal) salts such as potassium phosphites e.g. $KH_2PO_3$ and $K_2HPO_3$, sodium phosphites and ammonium phosphites, and ($C_1$-$C_4$) alkyl esters of phosphorous acid and their salts such as aluminum ethyl phosphite (fosetyl-Al), calcium ethyl phosphite, magnesium isopropyl phosphite, magnesium isobutyl phosphite, magnesium sec-butyl phosphite and aluminum N-butyl phosphite. Of course, mixtures of phosphite containing compounds are also encompassed. A mixture of e.g. $KH_2PO_3$ and $K_2HPO_3$ can easily be obtained by e.g. adding KOH or $K_2CO_3$ to a final pH of 5.0-6.0 to a $KH_2PO_3$ solution. As indicated above, precursor-type compounds which in the crop or plant are metabolized into phosphite compounds can also be included in the compositions of the present invention. Examples are phosphonates such as the fosetyl-aluminium complex. In e.g. a crop or plant the ethyl phosphonate part of this molecule is metabolized into a phosphite. An example of such a compound in the commercial ethyl hydrogen phosphonate product called Aliette® (Bayer, Germany). The ratio of phosphite to natamycin (in weight) in the compositions is in general between 2:1 to 500:1 (w/w), preferably between 3:1 to 300:1 (w/w) and more preferably between 5:1 to 200:1 (w/w).

Compositions according to the invention may have a pH of from 1 to 10, preferably of from 2 to 9, more preferably of from 3 to 8 and most preferably of from 4 to 7. They may be solid, e.g. powder compositions, or may be liquid. The compositions of the present invention can be aqueous or non-aqueous ready-to-use compositions, but may also be aqueous or non-aqueous concentrated compositions/suspensions or stock compositions, suspensions and/or solutions which before use have to be diluted with a suitable diluent such as water or a buffer system. Alternatively, the compositions of the invention can also be used to prepare coating emulsions. The compositions of the present invention can also have the form of concentrated dry products such as e.g. powders, granulates and tablets. They can be used to prepare compositions for immersion or spraying of products such as agricultural products including plants, crops, vegetables and/or fruits. Of course, the above is also applicable when the polyene antifungal compound and the at least one antifungal compound from the family of pyrazole fungicides are applied as separate compositions.

In a further aspect the invention relates to a kit comprising a polyene antifungal compound and at least one antifungal compound from the family of pyrazole fungicides. The polyene antifungal compound and the at least one antifungal compound from the family of pyrazole fungicides may be present in two separate packages, e.g. containers. The components of the kit may be either in dry form or liquid form in the package. If necessary, the kit may comprise instructions for dissolving the compounds. In addition, the kit may contain instructions for applying the compounds.

In a further aspect the invention pertains to a method for protecting a product against fungi by treating the agricultural product with a polyene antifungal compound and at least one antifungal compound from the family of pyrazole fungicides. In addition, the product can be treated with other antifungal and/or antimicrobial compounds either prior to, concomitant with or after treatment of the products with the polyene antifungal compound and the at least one antifungal compound from the family of pyrazole fungicides. The product may be treated by sequential application of the polyene antifungal compound and the at least one antifungal compound from the family of pyrazole fungicides or vice versa. Alternatively, the product may be treated by simultaneous application of the polyene antifungal compound and the at least one antifungal compound from the family of pyrazole fungicides. In case of simultaneous application, the compounds can be present in different compositions that are applied simultaneously or the compounds may be present in a single composition. In yet another embodiment the product may be treated by separate or alternate modes of applying the antifungal compounds. In an embodiment the invention is directed to a process for the treatment of products by applying the polyene antifungal compound and the at least one antifungal compound from the family of pyrazole fungicides to the products. By applying the compounds fungal growth on or in the products can be prevented. In other words, the compounds protect the products from fungal growth and/or from fungal infection and/or from fungal spoilage. The compounds can also be used to treat products that have been infected with a fungus. By applying the compounds the disease development due to fungi on or in these products can be slowed down, stopped or the products may even be cured from the disease. In an embodiment of the invention the products are treated with a composition or kit according to the invention. In an embodiment the product is a food, feed, pharmaceutical, cosmetic or agricultural product. In a preferred embodiment the product is an agricultural product.

The polyene antifungal compound and the at least one antifungal compound from the family of pyrazole fungicides, the compositions according to the invention and the kits according to the invention can be applied to the products by spraying. Other methods suitable for applying these compounds, compositions and kits in liquid form to the products are also a part of the present invention. These include, but are not limited to, dipping, watering, drenching, introduction into a dump tank, vaporizing, atomizing, fogging, fumigating, painting, brushing, dusting, foaming, spreading-on, packaging and coating (e.g. by means of wax or electrostatically). In addition, the antifungal compounds may also be injected into the soil. Spraying applications using automatic systems are known to reduce the labour costs and are cost-effective. Methods and equipment well-known to a person skilled in the art can be used for that purpose. The compositions according to the invention can be regularly sprayed, when the risk of infection is high. When the risk of infection is lower spray intervals may be longer. Depending on the type of application, the amount of polyene antifungal compound applied may vary from 5 ppm to 10,000 ppm, preferably from 10 ppm to 5,000 ppm and most preferably from 20 to 1,000 ppm. Depending on the type of application, the amount of the at least one antifungal compound from the family of pyrazole fungicides applied may vary from 10 ppm to 5,000 ppm, preferably from 20 ppm to 3,000 ppm and most preferably from 50 to 1,000 ppm.

In a specific embodiment the agricultural product can be treated post-harvest. By using a polyene antifungal compound and the at least one antifungal compound from the family of pyrazole fungicides the control of post-harvest and/or storage diseases is achieved for a long period of time to allow transport of the harvested agricultural product over long distances and under various storage conditions with different controlled atmosphere systems in respect of temperature and humidity. Post-harvest storage disorders are e.g. lenticel spots, scorch, senescent breakdown, bitter pit, scald, water core, browning, vascular breakdown, $CO_2$ injury, $CO_2$ or $O_2$ deficiency, and softening. Fungal diseases may be caused for example by the following fungi: *Mycosphaerella* spp., *Mycosphaerella musae, Mycosphaerella fragariae, Mycosphaerella citri; Mucor* spp., e.g. *Mucor piriformis; Monilinia* spp., e.g. *Monilinia fructigena, Monilinia laxa; Phomopsis* spp., *Phomopsis natalensis; Colletotrichum* spp., e.g. *Colletotrichum musae, Colletotrichum gloeosporioides, Colletotrichum coccodes; Verticillium* spp., e.g. *Verticillium theobromae; Nigrospora* spp.; *Botrytis* spp., e.g. *Botrytis cinerea; Dipodia* spp., e.g. *Dipodia citri; Pezicula* spp.; *Alternaria* spp., e.g. *Alternaria citri, Alternaria alternata; Septoria* spp., e.g. *Septoria depressa; Venturia* spp., e.g. *Venturia inaequalis, Venturia pyrina; Rhizopus* spp., e.g. *Rhizopus stolonifer, Rhizopus oryzae; Glomerella* spp., e.g. *Glomerella cingulata; Sclerotinia* spp., e.g. *Sclerotinia fruiticola; Ceratocystis* spp., e.g. *Ceratocystis paradoxa; Fusarium* spp., e.g. *Fusarium semitectum, Fusarium moniliforme, Fusarium solani, Fusarium oxysporum; Cladosporium* spp., e.g. *Cladosporium fulvum, Cladosporium cladosporioides, Cladosporium cucumerinum, Cladosporium musae; Penicillium* spp., e.g. *Penicillium funiculosum, Penicillium expansum, Penicillium digitatum, Penicillium italicum; Phytophthora* spp., e.g. *Phytophthora citrophthora, Phytophthora fragariae, Phytophthora cactorum, Phytophthora parasitica; Phacydiopycnis* spp., e.g. *Phacydiopycnis malirum; Gloeosporium* spp., e.g. *Gloeosporium album, Gloeosporium perennans, Gloeosporium fructigenum, Gloeosporium singulata; Geotrichum* spp., e.g. *Geotrichum candidum; Phlyctaena* spp., e.g. *Phlyctaena vagabunda; Cylindrocarpon* spp., e.g. *Cylindrocarpon mali; Stemphyllium* spp., e.g. *Stemphyllium vesicarium; Thielaviopsis* spp., e.g. *Thielaviopsis paradoxy; Aspergillus* spp., e.g. *Aspergillus niger, Aspergillus carbonarius; Nectria* spp., e.g. *Nectria galligena; Cercospora* spp., e.g. *Cercospora angreci, Cercospora apii, Cercospora atrofiliformis, Cercospora musae, Cercospora zeaemaydis.*

Another aspect of the present invention relates to the use of a polyene antifungal compound and at least one antifungal compound from the family of pyrazole fungicides to protect a product against fungi. As indicated above, the compounds may be used, e.g. applied, sequentially or simultaneously. In an embodiment the invention relates to a use, wherein a composition or kit according to the invention is applied to the product. In an embodiment the product is a food, feed, pharmaceutical, cosmetic or agricultural product. In a preferred embodiment the product is an agricultural product.

In a specific embodiment the polyene antifungal compound and at least one antifungal compound from the family of pyrazole fungicides can be used in medicine, e.g. to treat and/or prevent fungal diseases. The polyene antifungal compound and at least one antifungal compound from the family of pyrazole fungicides can for instance be used in the form of a pharmaceutical composition. The composition may further comprise pharmaceutically acceptable excipients. The antifungal compounds may be administered orally or parenterally. The type of composition is dependent on the route of administration.

A further aspect of the invention is directed to a product treated with a polyene antifungal compound and at least one antifungal compound from the family of pyrazole fungicides. In an embodiment the product is treated with a composition or kit according to the invention. The invention is therefore directed to a product comprising a polyene antifungal compound and at least one antifungal compound from the family of pyrazole fungicides. The treated products may comprise a polyene antifungal compound and at least one antifungal compound from the family of pyrazole fungicides on their surface and/or inside the product. Alternatively, the treated products may comprise a coating comprising these compounds. In an embodiment the treated products comprise from 0.000001 to 200 $mg/dm^2$, preferably 0.00001 to 100 $mg/dm^2$, more preferably from 0.00005 to 10 $mg/dm^2$ of the polyene antifungal compound on their surface. In a further embodiment they comprise from 0.000001 to 200 $mg/dm^2$, preferably 0.00001 to 100 $mg/dm^2$, more preferably from 0.00005 to 10 $mg/dm^2$ of the at least one antifungal compound from the family of pyrazole fungicides on their surface. In an embodiment the product is a food, feed, pharmaceutical, cosmetic or agricultural product. In a preferred embodiment the product is an agricultural product.

The term "food products" as used herein is to be understood in a very broad sense and includes, but is not limited to, cheese, cream cheese, shredded cheese, cottage cheese processed cheese, sour cream, dried fermented meat product including salamis and other sausages, wine, beer, yoghurt, juice and other beverages, salad dressing, cottage cheese dressing, dips, bakery products and bakery fillings, surface glazes and icing, spreads, pizza toppings, confectionery and confectionery fillings, olives, olive brine, olive oil, juices, tomato purees and paste, condiments, and fruit pulp and the like food products.

The term "feed products" as used herein is also to be understood in a very broad sense and includes, but is not limited to, pet food, broiler feed, etc.

The term "pharmaceutical product" as used herein is also to be understood in a very broad sense and includes products comprising an active molecule such as a drug, agent, or pharmaceutical compound and optionally a pharmaceutically acceptable excipient, i.e. any inert substance that is combined with the active molecule for preparing an agreeable or convenient dosage form.

The term "cosmetic product" as used herein is also to be understood in a very broad sense and includes products that are used for protecting or treating horny tissues such as skin and lips, hair and nails from drying by preventing transpiration of moisture thereof and further conditioning the tissues as well as giving good appearance to these tissues. Products contemplated by the term "cosmetic product" include, but are not limited to, moisturizers, personal cleansing products, occlusive drug delivery patches, nail polish, powders, wipes, hair conditioners, skin treatment emulsions, shaving creams and the like.

The term "agricultural products" as used herein is also to be understood in a very broad sense and includes, but is not limited to, cereals, e.g. wheat, barley, rye, oats, rice, sorghum and the like; beets, e.g. sugar beet and fodder beet; pome and stone fruit and berries, e.g. apples, pears, plums, apricots, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes, aubergines; fibrous plants, e.g. cotton, flax, hemp, jute; citrus fruit, e.g. oranges, lemons, grapefruits, mandarins, limes; tropical fruit, e.g. papayas, passion fruit, mangos, carambolas, pineapples, bananas, kiwis; vegetables, e.g. spinach, lettuce, asparagus, brassicaceae such as cabbages and turnips, carrots, onions, tomatoes, potatoes, seed-potatoes, hot and sweet peppers; laurel-like plants, e.g. avocado, cinnamon, camphor tree; or products such as maize, tobacco, nuts, coffee, sugarcane, tea, grapevines, hops, rubber plants, as well as ornamental plants, e.g. cut flowers, roses, tulips, lilies, narcissus, crocuses, hyacinths, dahlias, gerbera, carnations, fuchsias, chrysanthemums, and flower bulbs, shrubs, deciduous trees and evergreen trees such as conifers, plants and trees in greenhouses. It includes, but is not limited to, plants and their parts, fruits, seeds, cuttings, cultivars, grafts, bulbs, tubers, root-tubers, rootstocks, cut flowers and vegetables.

A method for preparing a composition as described herein is another aspect of the present invention. The method comprises adding a polyene antifungal compound to at least one antifungal compound from the family of pyrazole fungicides. The compounds may for instance be added separately to an aqueous composition and mixed, followed, if necessary, by adjustment of the pH, viscosity, etc. If added separately, some or all of the separate compounds may be in powder form, but alternatively some or all may also be in liquid form. The compounds may for instance also be added to one another in powder form and mixed to obtain a powdered composition. The powdered composition may then be added to an aqueous composition.

EXAMPLES

Example 1

Pre-Harvest Application

Leaves of banana plants are inoculated with fungi. As a control non-inoculated leaves are also included. Next, a defined part of the leaves are treated with composition 1 (natamycin), composition 2 (bixafen), composition 3 (fenpyrazamine), composition 4 (fluxapyroxad), composition 5 (furametpyr), composition 6 (isopyrazam), composition 7 (penflufen), composition 8 (penthiopyrad), composition 9 (rabenzazole), composition 10 (sedaxane), composition 11 (natamycin+bixafen), composition 12 (natamycin+fenpyrazamine), composition 13 (natamycin+fluxapyroxad), composition 14 (natamycin+furametpyr), composition 15 (natamycin+isopyrazam), composition 16 (natamycin+penflufen), composition 17 (natamycin+penthiopyrad), composition 18 (natamycin+rabenzazole), or composition 19 (natamycin+sedaxane). Each composition is applied by spraying. Untreated leaves are also included (untreated control).

The obtained results show that the compositions of the present invention protect banana plants from fungal growth and further demonstrate that the compositions of the present invention show a synergistically enhanced activity compared to the activity of the active compounds when applied individually.

Example 2

Post-Harvest Application

Bananas are injured according to the method described by de Lapeyre de Bellaire and Dubois (1987). Bananas are wounded using a cork borer followed by contamination with fungal spores. After incubation for several hours at room temperature, the bananas are dipped in one of the following compositions: a) no treatment (control 1), b) dipped in water (control 2), c) dipped in natamycin, d) dipped in bixafen, e) dipped in fenpyrazamine, f) dipped in fluxapyroxad, g) dipped in furametpyr, h) dipped in isopyrazam, i) dipped in penflufen, j) dipped in penthiopyrad, k) dipped in rabenzazole, l) dipped in sedaxane, m) dipped in natamycin+bixafen, n) dipped in natamycin+fenpyrazamine, o) dipped in natamycin+fluxapyroxad, p) dipped in natamycin+furametpyr, q) dipped in natamycin+isopyrazam, r) dipped in natamycin+penflufen, s) dipped in natamycin+penthiopyrad, t) dipped in natamycin+rabenzazole, u) dipped in natamycin+sedaxane. After this treatment the bananas are incubated in closed boxes at 21° C. at elevated humidity. Each day the bananas are judged visually on fungal development.

The results show that the composition comprising natamycin and at least one antifungal compound from the family of pyrazole fungicides protects bananas better against fungi than natamycin or at least one antifungal compound from the family of pyrazole fungicides alone. Surprisingly, the combined application of natamycin and at least one antifungal compound from the family of pyrazole fungicides leads to a strong synergistic reduction in infection.

Example 3

Treatment of Strawberries

Ten fresh, organic strawberries were used per treatment. Each strawberry was wounded with a 0.5 mm long cut and each wound was inoculated with 10 µl of a *Botrytis cinerea* suspension containing $1 \times 10^5$ of spores/ml. After a 2-hour incubation period at 20° C., each strawberry was dipped individually for 1 minute in a freshly prepared aqueous antifungal composition comprising either 500 ppm natamycin (DSM Food Specialties, Delft, The Netherlands), 2000 ppm bixafen or both. The antifungal compositions also comprised 3.1% (w/w) beeswax, 0.76% (w/w) glycerol, 0.66% (w/w) polyoxyethylene sorbitan monostearate (Tween 60), 0.03% (w/w) methylhydroxyethylcellulose (MHEC), 0.02% (w/w) xanthan gum, 0.02% (w/w) anti-foaming agent, 0.15% (w/w) citric acid and 0.01% (w/w) potassium sorbate. The pH of the compositions was 4. A composition without natamycin or bixafen was used as control. The treated strawberries were incubated in a closed box in the dark at 20° C.

During incubation, mould growth on the strawberries was assessed in a twofold manner: (i) the number of moulded strawberries per total of 10 strawberries was counted; and (ii) the antifungal activity (in %) of the individual and combined active ingredients was determined by calculating the reduction in mould growth observed on the strawberries treated with the antifungal composition in comparison to the mould growth on the strawberries treated with the control composition. The expected antifungal activity (E in %) of the combined antifungal composition comprising both active ingredients was calculated according to the Colby equation (Colby, 1967):

$$E = X + Y - [(X \cdot Y)/100]$$

wherein X and Y are the observed antifungal activities (in %) of the individual active ingredients X and Y, respectively. If the observed antifungal activity (O in %) of the combination exceeds the expected antifungal activity (E in %) of the combination and the synergy factor O/E is thus >1.0, the combined application of the active ingredients leads to a synergistic antifungal effect.

The results in Table 1 (number of moulded strawberries per total of 10 strawberries) and Table 2 (antifungal activity) clearly demonstrate that the antifungal composition comprising 500 ppm natamycin and 2000 ppm bixafen had a much stronger antifungal effect on strawberries than natamycin or bixafen alone.

During 3 through 6 days of incubation, all 10 strawberries treated with either the control composition or natamycin alone showed mould growth. When bixafen was used for treatment, 8 and 9 of the 10 strawberries were moulded on day 3 and 4, respectively, as were all 10 strawberries on days 5 and 6. However, of the 10 strawberries treated with the composition comprising both natamycin and bixafen, mould growth was observed for only 4 strawberries on day 3, 5 strawberries on day 4 and 8 strawberries on days 5 and 6 (see Table 1). Furthermore, the observed antifungal activity of the composition comprising both natamycin and bixafen exceeded the expected antifungal activity with 15 to 27% between 3 and 9 days of incubation. The corresponding synergy factor increased from 1.2 on day 3 to 6.0 on day 9 (see Table 2).

Hence, the combined application of 500 ppm natamycin and 2000 ppm bixafen has a remarkably strong synergistic antifungal effect on strawberries.

Example 4

Treatment of Strawberries

The experiment was conducted as described in Example 3, except for the fact that each strawberry was first wounded, then incubated for 2 hours at 20° C. and subsequently dipped individually for 1 minute in a freshly prepared aqueous antifungal composition comprising either 500 ppm natamycin (DSM Food Specialties, Delft, The Netherlands), 1000 ppm bixafen or both. After treatment, each strawberry was inoculated with 10 µl of a *Botrytis cinerea* suspension containing $1 \times 10^5$ of spores/ml. The treated strawberries were assessed on mould growth according to the two methods described in Example 3.

The results in Table 3 (antifungal activity) and Table 4 (number of moulded strawberries per total of 10 strawberries) reveal that the antifungal composition comprising 500 ppm natamycin as well as 1000 ppm bixafen was more successful in limiting mould growth on strawberries than the compositions comprising natamycin or bixafen individually.

After 3 days of incubation, the observed antifungal activity was 8% higher than the expected antifungal activity, which resulted in a synergy factor >1.0 (see Table 3).

After 5 days of incubation, all 10 strawberries treated with either the control composition or natamycin alone were moulded, as were 8 of the 10 strawberries treated with bixafen alone. However, when the active ingredient combination of natamycin and bixafen was applied on the strawberries, mould growth was observed for only 5 of the 10 strawberries on day 5 (see Table 4). Moreover, the observed antifungal activity of the composition comprising natamycin and bixafen exceeded the expected antifungal activity with 16 and 18% on day 5 and 6, respectively. Consequently, the obtained synergy factor was >1.0 on both days (see Table 3).

In conclusion, the results of this example prove that the combined application of 500 ppm natamycin and 1000 ppm bixafen synergistically reduces mould growth on strawberries.

Example 5

Treatment of Strawberries

The experiment was conducted as described in Example 3, except for the fact that each wounded and inoculated strawberry was dipped individually for 1 minute in a freshly prepared aqueous antifungal composition comprising either 250 ppm natamycin (DSM Food Specialties, Delft, The Netherlands), 500 ppm bixafen or both. The treated strawberries were assessed on mould growth. The antifungal activity (in %) of the individual and combined active ingredients was determined according to the method described in Example 3.

The results in Table 5 show that the antifungal composition comprising 250 ppm natamycin as well as 500 ppm bixafen was superior to the compositions comprising either natamycin alone or bixafen alone in reducing mould growth on strawberries.

After 4, 6, 7, 9 and 10 days of incubation, the observed antifungal activity was 10 to 20% higher than the expected antifungal activity and the corresponding synergy factors increased from 1.2 on day 4 to >10 on day 10 (see Table 5).

Thus, strong synergistic activity against fungi exists between 250 ppm natamycin and 500 ppm bixafen when applied in combination on strawberries.

Example 6

Treatment of Strawberries

The experiment was conducted as described in Example 3, except for the fact that each wounded and inoculated strawberry was dipped individually for 1 minute in a freshly prepared aqueous antifungal composition comprising either 250 ppm natamycin (DSM Food Specialties, Delft, The Netherlands), 250 ppm bixafen or both. The treated strawberries were incubated for one week and, as of day 3, assessed on mould growth daily according to the one or both methods described in Example 3.

The results in Table 6 (number of moulded strawberries per total of 10 strawberries) and Table 7 (antifungal activity) unequivocally demonstrate that the combined antifungal composition comprising 250 ppm natamycin and 250 ppm bixafen protected strawberries more effectively against mould growth than the compositions comprising natamycin or bixafen individually.

After 3 days of incubation, all 10 strawberries treated with the control composition were moulded, as were respectively 8 of the 10 strawberries treated with natamycin alone and 9 of the 10 strawberries treated with bixafen alone. However, only 5 of the 10 strawberries treated with the composition comprising natamycin and bixafen showed mould growth on day 3 (see Table 6).

After 4 and 5 days of incubation, all 10 strawberries treated with either the control composition or natamycin alone were moulded, as were respectively 9 and 10 of the 10 strawberries treated with bixafen, respectively. However, of the 10 strawberries treated with the active ingredient combination of natamycin and bixafen, mould growth was observed for only 7 strawberries on day 4 and 8 strawberries on day 5 (see Table 6). Furthermore, the observed antifungal activity exceeded the expected antifungal activity with 13% to 21% between 4 and 7 days of incubation. The corresponding synergy factor therefore increased from 1.3 on day 4 to 2.3 on day 7 (see Table 7).

Thus, the combined application of 250 ppm natamycin and 250 ppm bixafen leads to a strong synergistic reduction in mould growth on strawberries.

Example 7

Treatment of Mandarins

Ten fresh, organic mandarins were used per treatment. The peel of each mandarin was wounded once using a cork borer according to the method described by de Lapeyre de Bellaire and Dubois (1987). Subsequently, each wound was inoculated with 10 µl of a *Penicillium italicum* suspension containing $1 \times 10^5$ of spores/ml. After incubation for 2 hours at 20° C., the mandarins were dipped individually for 1 minute in a freshly prepared aqueous antifungal composition comprising either 500 ppm natamycin (DSM Food Specialties, Delft, The Netherlands), 2000 ppm bixafen or both. In addition, the antifungal compositions comprised 3.1% (w/w) beeswax, 0.76% (w/w) glycerol, 0.66% (w/w) polyoxyethylene sorbitan monostearate (Tween 60), 0.03% (w/w) methylhydroxyethylcellulose (MHEC), 0.02% (w/w) xanthan gum, 0.02% (w/w) anti-foaming agent, 0.15% (w/w) citric acid and 0.01% (w/w) potassium sorbate. The pH of the compositions was 4. A composition without natamycin or bixafen was used as control.

The treated mandarins were incubated in a closed box in the dark at 20° C. and assessed on mould growth during incubation. The antifungal activity (in %) of the individual and combined active ingredients was determined by calculating the reduction in mould growth observed on the mandarins treated with the antifungal composition in comparison to the mould growth on the mandarins treated with the control composition according to the Colby method (Colby, 1967) described in Example 3.

The results in Table 8 prove that the active ingredient combination of 500 ppm natamycin and 2000 ppm bixafen was more successful in limiting mould growth on mandarins than natamycin or bixafen individually.

After 4, 6, 9, 11, 14 and 15 days of incubation, the observed antifungal activity of composition comprising natamycin and bixafen exceeded the expected antifungal activity with 6 to 13%. The corresponding synergy factor was >1.0 on each of the aforementioned days and ranged from 1.2 on day 4 to 2.8 on day 15 (see Table 8).

In conclusion, the results of this example clearly demonstrate the synergistic antifungal effect of 500 ppm natamycin and 2000 ppm bixafen when applied in combination on mandarins.

Example 8

Treatment of Mandarins

The experiment was conducted as described in Example 7, except for the fact that each wounded, inoculated mandarin was dipped individually for 1 minute in a freshly prepared aqueous antifungal composition comprising either 500 ppm natamycin (DSM Food Specialties, Delft, The Netherlands), 1000 ppm bixafen or both. The antifungal activity (in %) of the individual and combined active ingredients on mandarins was assessed according to the Colby method (Colby, 1967) described in Example 3.

The results (see Table 9) reveal that the antifungal composition comprising 500 ppm natamycin and 1000 ppm bixafen had a stronger antifungal activity on mandarins than natamycin or bixafen alone.

After 4, 6, 7, 9, 14 and 15 days of incubation, the observed antifungal activity of the active ingredient combination of natamycin and bixafen was between 7 and 14% higher than the expected antifungal activity and the synergy factor ranged from 1.2 to 3.0 (see Table 9).

It can therefore be concluded that the combined application of 500 ppm natamycin and 1000 ppm bixafen leads to a synergistic reduction in mould growth on mandarins.

Example 9

Treatment of Mandarins

The experiment was conducted as described in Example 7, except for the fact that each wounded, inoculated mandarin was dipped individually for 1 minute in a freshly prepared aqueous antifungal composition comprising either 250 ppm natamycin (DSM Food Specialties, Delft, The Netherlands), 500 ppm bixafen or both. The antifungal activity (in %) of the individual and combined active ingredients on mandarins was assessed according to the Colby method (Colby, 1967) described in Example 3.

The results (see Table 10) clearly demonstrate that the active ingredient combination of 250 ppm natamycin and 500 ppm bixafen had a higher efficacy against mould growth on mandarins than natamycin or bixafen individually.

After 4, 6, 7, 9, 11, 13 and 15 days of incubation, the observed antifungal activity of the composition comprising natamycin as well as bixafen exceeded the expected antifungal activity with 9 to 26%, which resulted in a synergy factor varying from 1.2 to 4.3 (see Table 10).

Thus, the combined application of 250 ppm natamycin and 500 ppm bixafen synergistically reduces mould growth on mandarins.

Example 10

Treatment of Mandarins

The experiment was conducted as described in Example 7, except for the fact that each wounded, inoculated mandarin was dipped individually for 1 minute in a freshly prepared aqueous antifungal composition comprising either 250 ppm natamycin (DSM Food Specialties, Delft, The Netherlands), 250 ppm bixafen or both. The antifungal activity (in %) of the individual and combined active ingredients on mandarins was assessed according to the Colby method (Colby, 1967) described in Example 3.

The results (see Table 11) prove that the composition comprising 250 ppm natamycin and 250 ppm bixafen was superior to the compositions comprising either natamycin alone or bixafen alone in reducing mould growth on mandarins.

After 3, 4, 6, 7 and 9 days of incubation, the observed antifungal activity of the composition comprising natamycin as well as bixafen was 10 to 29% higher than the expected antifungal. Consequently, the synergy factor on each of the aforementioned days exceeded >1.0 and increased from 1.1 on day 3 to 3.3 on day 9 (see Table 11).

Hence, synergistic activity against fungi exists between 250 ppm natamycin and 250 ppm bixafen when applied in combination on mandarins.

Example 11

Treatment of Apples

Ten fresh, organic apples were used per treatment. Each apple was wounded once using a cork borer according to the method described by de Lapeyre de Bellaire and Dubois (1987). Subsequently, each wound was inoculated with 10 µl of a *Penicillium italicum* suspension containing $1 \times 10^6$ of spores/ml. After incubation for 2 hours at 20° C., the apples were dipped individually for 1 minute in a freshly prepared aqueous antifungal composition comprising either 500 ppm natamycin (DSM Food Specialties, Delft, The Netherlands), 2000 ppm bixafen or both. In addition, the antifungal compositions comprised 3.1% (w/w) beeswax, 0.76% (w/w) glycerol, 0.66% (w/w) polyoxyethylene sorbitan monostearate (Tween 60), 0.03% (w/w) methylhydroxyethylcellulose (MHEC), 0.02% (w/w) xanthan gum, 0.02% (w/w) antifoaming agent, 0.15% (w/w) citric acid and 0.01% (w/w) potassium sorbate. The pH of the compositions was 4. A composition without natamycin or bixafen was used as control. The treated apples were incubated in a closed box in the dark at 20° C.

During incubation, the mould growth on the apples was assessed in a twofold manner: (i) the number of moulded apples per total of 10 apples was counted; and (ii) the antifungal activity (in %) of the individual and combined active ingredients was determined by calculating the reduction in mould growth observed on the apples treated with the antifungal composition in comparison to the mould growth on the apples treated with the control composition according to the Colby method described in Example 3 (Colby, 1967).

The results in Table 12 (number of moulded apples per total of 10 apples) and Table 13 (antifungal activity) reveal that the antifungal activity of the composition comprising 500 ppm natamycin and 2000 ppm bixafen was stronger than those of the compositions comprising natamycin or bixafen alone.

After 3 and 4 days of incubation, all 10 apples treated with the control composition were moulded, as were 9 of the 10 apples treated with natamycin alone and of the 10 apples treated with bixafen alone. However, mould growth on day 3 and 4 was observed for only 2 of the 10 apples treated with the combined composition comprising natamycin and bixafen (see Table 12).

After 6 and 7 days of incubation, all 10 apples treated with either the control composition or natamycin alone showed mould growth, as did 8 of the 10 apples treated with bixafen alone. However, treatment of 10 apples with the composition comprising both natamycin and bixafen resulted in only 2 and 4 moulded apples on day 6 and 7, respectively (see Table 12).

During 9 through 14 days of incubation, all apples treated with either the control composition, natamycin alone or bixafen alone were moulded, whereas mould growth was observed for only 6 of the 10 apples treated with the active ingredient combination of natamycin and bixafen (see Table 12).

Moreover, the observed antifungal activity of the active ingredient combination of natamycin and bixafen exceeded the expected antifungal activity with 14% on day 3, almost 50% on day 6 and approximately 30% on day 9 through 14. During this incubation period from 3 to 14 days, the synergy factor always exceeded >1.0 and ranged from 1.2 to 2.1 (see Table 13).

In conclusion, a surprisingly strong antifungal activity exists between 500 ppm natamycin and 2000 ppm bixafen when applied in combination on apples.

Example 12

Treatment of Apples

The experiment was conducted as described in Example 11, except for the fact that each wounded and inoculated apple was dipped individually for 1 minute in a freshly prepared aqueous antifungal composition comprising either 500 ppm natamycin (DSM Food Specialties, Delft, The Netherlands), 1000 ppm bixafen or both. During incubation, the treated apples were assessed on mould growth according to the two methods described in Example 3.

The results in Table 14 (number of moulded apples per total of 10 apples) and Table 15 (antifungal activity) reveal that that the antifungal composition comprising 500 ppm natamycin as well as 1000 ppm bixafen was more successful in limiting mould growth on apples than the compositions comprising natamycin or bixafen individually.

After 3 and 4 days of incubation, all 10 apples treated with the control composition were moulded, as were 9 of the 10 apples treated with natamycin alone and 6 of the 10 apples treated with bixafen alone. However, of the 10 apples treated with the combined composition comprising natamycin and bixafen, only 2 and 3 were moulded on day 3 and 4, respectively (see Table 14).

After 6 and 7 days of incubation, all 10 apples treated with either the control composition or natamycin alone showed mould growth, as did respectively 8 and 9 of the apples treated with bixafen alone, respectively. However, treatment of 10 apples with the composition comprising both natamycin and bixafen resulted in only 4 moulded apples on day 6 and 5 moulded apples on day 7 (see Table 14).

During 9 through 14 days of incubation, all apples treated with either the control composition, natamycin alone or bixafen alone were moulded, whereas mould growth was observed for only 6 of the 10 apples treated with the active ingredient combination of natamycin and bixafen (see Table 14).

Moreover, the observed antifungal activity of the combined composition comprising natamycin and bixafen exceeded the expected antifungal activity with 23 to >30% during 3 and 14 days of incubation. The synergy factor was continuously >1.0 during the aforementioned incubation period and increased from 1.4 on day 3 to 1.7 on day 14 (see Table 15).

The results of this example clearly show that the combined application of 500 ppm natamycin and 1000 ppm bixafen synergistically reduces mould growth on apples.

Example 13

Treatment of Apples

The experiment was conducted as described in Example 11, except for the fact that each wounded and inoculated apple was dipped individually for 1 minute in a freshly prepared aqueous antifungal composition comprising either 250 ppm natamycin (DSM Food Specialties, Delft, The Netherlands), 500 ppm bixafen or both. After 6, 7 and 9 days of incubation, the treated apples were assessed on mould growth according to the two methods described in Example 3.

The results in Table 16 (number of moulded apples per total of 10 apples) and Table 17 (antifungal activity) reveal that that the antifungal composition comprising both 250 ppm natamycin and 500 ppm bixafen more effectively limited mould growth on apples than natamycin or alone.

After 6, 7 and 9 days of incubation, all 10 apples treated with either the control composition, natamycin alone or bixafen alone showed mould growth. However, of the apples treated with the active ingredient combination of natamycin and bixafen, only 5, 6 and 8 were moulded on day 6, 7, and 9, respectively (see Table 16). Furthermore, the observed antifungal activity of the combined composition comprising natamycin and bixafen exceeded the expected antifungal activity with 13% on day 6, 9% on day 7 and 12% on day 9, which resulted in synergy factor >1.0 on each of these days (see Table 17).

It can therefore be concluded that the combined application of 250 ppm natamycin and 500 ppm bixafen leads to a synergistic reduction in mould growth on apples.

Example 14

Treatment of Apples

The experiment was conducted as described in Example 11, except for the fact that each wounded and inoculated apple was dipped individually for 1 minute in a freshly prepared aqueous antifungal composition comprising either 250 ppm natamycin (DSM Food Specialties, Delft, The Netherlands), 250 ppm bixafen or both. During incubation, the treated apples were assessed on mould growth according to the two methods described in Example 3.

The results in Table 18 (number of moulded apples per total of 10 apples) and Table 19 (antifungal activity) prove that the activity of the composition comprising 250 ppm natamycin and 250 ppm bixafen against mould growth on apples was stronger than those of the compositions comprising natamycin or bixafen alone.

During 6 through 15 days of incubation, all apples treated with the control composition, natamycin alone or bixafen alone were moulded. However, when the composition comprising both bixafen and natamycin was used for treatment, 6 of 10 apples were moulded on day 6 through 9 and 7 of 10 apples were moulded on day 11 through 15 (see Table 18). Moreover, the observed antifungal activity of the active ingredient combination of natamycin and bixafen exceeded the expected antifungal activity with 18% on day 6, 32% on day 9, 25% on day 11 and 20% on day 14. The synergy factor was >1.0 on each of these days (see Table 19).

Thus, this example convincingly demonstrates the synergistic antifungal effect of the combined application of 250 ppm natamycin and 250 ppm bixafen on apples.

Example 15

In Vitro Antifungal Activity

To demonstrate synergistic antifungal activity of the combination of natamycin with isopyrazam against *Botrytis cinerea*, an in vitro assay was conducted using 96-well microtiter plates. The following compositions were tested:
 Control (no active ingredient),
 1.25 ppm natamycin (DSM Food Specialties, Delft, The Netherlands),
 6.25 ppm isopyrazam,
 1.25 ppm natamycin+6.25 ppm isopyrazam.

After filling each well of a microtiter plate with 84 µl of PCB medium, the active ingredient(s) were added from separate stock solutions prepared in PCB medium or methanol, which resulted in an intermediate volume of 100 µl per well. Subsequently, 100 µl of a *Botrytis cinerea* suspension prepared in PCB medium was used to inoculated each well with $2.5 \times 10^3$ spores/ml. Each well thus contained a final volume of 200 µl and <1% of methanol, which did not affect growth of *Botrytis cinerea* (data not shown).

After incubation of the microtiter plates at 25° C., the in vitro antifungal activity (%) of the individual active ingredients was assessed by calculating the reduction in mould growth observed in the presence of the active ingredient in comparison to the mould growth observed in the absence of the active ingredient. The expected antifungal activity (E in %) of the active ingredient combination was calculated according to the Colby equation (Colby, 1967):

$$E = X + Y - [(X \cdot Y)/100]$$

wherein X and Y are the observed antifungal activities (in %) of the individual active ingredients X and Y, respectively. If the observed antifungal activity (O in %) of the combination exceeds the expected antifungal activity (E in %) of the combination and the resulting synergy factor O/E is thus >1.0, the combined application of the active ingredients leads to a synergistic antifungal effect.

The results reveal that the active ingredient combination of natamycin and isopyrazam (see Table 20) was more effective in inhibiting growth of *Botrytis cinerea* than natamycin or isopyrazam individually. The observed antifungal activity of natamycin in combination with isopyrazam was 100% higher than the expected antifungal activity. Consequently, the corresponding synergy factor was much higher than 1.0.

Hence, the active ingredient combination of natamycin and isopyrazam synergistically inhibits growth of *Botrytis cinerea*.

Example 16

In Vitro Antifungal Activity

The experiment was conducted as described in Example 15, except for the fact that the following compositions were tested:
Control (no active ingredient),
0.63 or 1.25 ppm natamycin (DSM Food Specialties, Delft, The Netherlands),
25 ppm isopyrazam,
25 ppm bixafen,
0.63 ppm natamycin+25 ppm isopyrazam,
1.25 ppm natamycin+25 ppm bixafen.
Furthermore, *Penicillium italicum* was used for inoculation. The antifungal activity (in %) of the individual and combined active ingredients was determined according to the method described in Example 15.

The results (see Table 21) reveal that the active ingredient combinations natamycin+isopyrazam and natamycin+bixafen inhibited growth of *Penicillium italicum* more successfully than natamycin, isopyrazam or bixafen individually. The observed antifungal activities of the active ingredient combinations natamycin+isopyrazam and natamycin+bixafen exceeded the expected antifungal activities with 25%, which resulted in synergy factors >1.0.

Hence, the combined application of natamycin and isopyrazam as well as the combined application of natamycin and bixafen display synergistic antifungal activity against *Penicillium italicum*.

TABLE 1

Number of moulded strawberries incubated at 20° C. after treatment with compositions comprising either 500 ppm natamycin, 2000 ppm bixafen or both.

| Antifungal composition | Number of moulded strawberries/total number of 10 strawberries during incubation time (in days) | | |
|---|---|---|---|
| | Day 3 | Day 4 | Day 5-6 |
| Control | 10/10 | 10/10 | 10/10 |
| Natamycin 500 ppm | 10/10 | 10/10 | 10/10 |
| Bixafen 2000 ppm | 8/10 | 9/10 | 10/10 |
| Natamycin 500 ppm + bixafen 2000 ppm | 4/10 | 5/10 | 8/10 |

TABLE 2

Antifungal activity (%) of compositions comprising either 500 ppm natamycin, 2000 ppm bixafen or both on strawberries after incubation at 20° C.

| Antifungal composition | Incubation time (days) | Observed antifungal activity O (%) | Expected antifungal activity E (%) | Synergy factor O/E |
|---|---|---|---|---|
| Control | 3 | 0 | — | — |
| Natamycin 500 ppm | | 21 | — | — |
| Bixafen 2000 ppm | | 62 | — | — |
| Natamycin 500 ppm + bixafen 2000 ppm | | 85 | 70 | 1.2 |
| Control | 4 | 0 | — | — |
| Natamycin 500 ppm | | 16 | — | — |
| Bixafen 2000 ppm | | 55 | — | — |
| Natamycin 500 ppm + bixafen 2000 ppm | | 78 | 62 | 1.3 |
| Control | 5 | 0 | — | — |
| Natamycin 500 ppm | | 3 | — | — |
| Bixafen 2000 ppm | | 34 | — | — |
| Natamycin 500 ppm + bixafen 2000 ppm | | 64 | 37 | 1.7 |
| Control | 6 | 0 | — | — |
| Natamycin 500 ppm | | 0 | — | — |
| Bixafen 2000 ppm | | 27 | — | — |
| Natamycin 500 ppm + bixafen 2000 ppm | | 47 | 27 | 1.7 |
| Control | 7 | 0 | — | — |
| Natamycin 500 ppm | | 0 | — | — |
| Bixafen 2000 ppm | | 12 | — | — |
| Natamycin 500 ppm + bixafen 2000 ppm | | 33 | 12 | 2.8 |
| Control | 9 | 0 | — | — |
| Natamycin 500 ppm | | 0 | — | — |
| Bixafen 2000 ppm | | 3 | — | — |
| Natamycin 500 ppm + bixafen 2000 ppm | | 18 | 3 | 6.0 |

TABLE 3

Antifungal activity (%) of compositions comprising either 500 ppm natamycin, 1000 ppm bixafen or both on strawberries after incubation at 20° C.

| Antifungal composition | Incubation time (days) | Observed antifungal activity O (%) | Expected antifungal activity E (%) | Synergy factor O/E |
|---|---|---|---|---|
| Control | 3 | 0 | — | — |
| Natamycin 500 ppm | | 59 | — | — |
| Bixafen 1000 ppm | | 72 | — | — |
| Natamycin 500 ppm + bixafen 1000 ppm | | 97 | 89 | 1.1 |
| Control | 5 | 0 | — | — |
| Natamycin 500 ppm | | 19 | — | — |
| Bixafen 1000 ppm | | 55 | — | — |
| Natamycin 500 ppm + bixafen 1000 ppm | | 79 | 63 | 1.3 |
| Control | 6 | 0 | — | — |
| Natamycin 500 ppm | | 12 | — | — |
| Bixafen 1000 ppm | | 35 | — | — |
| Natamycin 500 ppm + bixafen 1000 ppm | | 61 | 43 | 1.4 |

TABLE 4

Number of moulded strawberries incubated at 20° C. after treatment with compositions comprising either 250 ppm natamycin, 1000 ppm bixafen or both.

| Antifungal composition | Incubation time (days) | Number of moulded wounds/total number of 10 wounds |
|---|---|---|
| Control | 5 | 10/10 |
| Natamycin 250 ppm | | 10/10 |
| Bixafen 1000 ppm | | 8/10 |
| Natamycin 250 ppm + bixafen 1000 ppm | | 5/10 |

TABLE 5

Antifungal activity (%) of compositions comprising either 250 ppm natamycin, 500 ppm bixafen or both on strawberries after incubation at 20° C.

| Antifungal composition | Incubation time (days) | Observed antifungal activity O (%) | Expected antifungal activity E (%) | Synergy factor O/E |
|---|---|---|---|---|
| Control | 4 | 0 | — | — |
| Natamycin 250 ppm | | 6 | — | — |
| Bixafen 500 ppm | | 65 | — | — |
| Natamycin 250 ppm + bixafen 500 ppm | | 78 | 67 | 1.2 |
| Control | 6 | 0 | — | — |
| Natamycin 250 ppm | | 0 | — | — |
| Bixafen 500 ppm | | 33 | — | — |
| Natamycin 250 ppm + bixafen 500 ppm | | 50 | 33 | 1.5 |
| Control | 7 | 0 | — | — |
| Natamycin 250 ppm | | 0 | — | — |
| Bixafen 500 ppm | | 12 | — | — |
| Natamycin 250 ppm + bixafen 500 ppm | | 32 | 12 | 2.7 |
| Control | 9 | 0 | — | — |
| Natamycin 250 ppm | | 0 | — | — |
| Bixafen 500 ppm | | 5 | — | — |
| Natamycin 250 ppm + bixafen 500 ppm | | 15 | 5 | 3.0 |
| Control | 10 | 0 | — | — |
| Natamycin 250 ppm | | 0 | — | — |
| Bixafen 500 ppm | | 0 | — | — |
| Natamycin 250 ppm + bixafen 500 ppm | | 10 | 0 | >10 |

TABLE 6

Number of moulded strawberries incubated at 20° C. after treatment with compositions comprising 250 ppm natamycin, 250 ppm bixafen or both.

| Antifungal composition | Number of moulded strawberries/total number of 10 strawberries during incubation time (in days) | | |
|---|---|---|---|
| | Day 3 | Day 4 | Day 5 |
| Control | 10/10 | 10/10 | 10/10 |
| Natamycin 250 ppm | 8/10 | 10/10 | 10/10 |
| Bixafen 250 ppm | 9/10 | 9/10 | 10/10 |
| Natamycin 250 ppm + bixafen 250 ppm | 5/10 | 7/10 | 8/10 |

TABLE 7

Antifungal activity (%) of compositions comprising either 250 ppm natamycin, 250 ppm bixafen or both on strawberries after incubation at 20° C.

| Antifungal composition | Incubation time (days) | Observed antifungal activity O (%) | Expected antifungal activity E (%) | Synergy factor O/E |
|---|---|---|---|---|
| Control | 4 | 0 | — | — |
| Natamycin 250 ppm | | 6 | — | — |
| Bixafen 250 ppm | | 47 | — | — |
| Natamycin 250 ppm + bixafen 250 ppm | | 67 | 50 | 1.3 |
| Control | 5 | 0 | — | — |
| Natamycin 250 ppm | | 2 | — | — |
| Bixafen 250 ppm | | 33 | — | — |
| Natamycin 250 ppm + bixafen 250 ppm | | 55 | 34 | 1.6 |
| Control | 6 | 0 | — | — |
| Natamycin 250 ppm | | 0 | — | — |
| Bixafen 250 ppm | | 23 | — | — |
| Natamycin 250 ppm + bixafen 250 ppm | | 40 | 23 | 1.7 |
| Control | 7 | 0 | — | — |
| Natamycin 250 ppm | | 0 | — | — |
| Bixafen 250 ppm | | 10 | — | — |
| Natamycin 250 ppm + bixafen 250 ppm | | 23 | 10 | 2.3 |

TABLE 8

Antifungal activity (%) of compositions comprising either 500 ppm natamycin, 2000 ppm bixafen or both on mandarins after incubation at 20° C.

| Antifungal composition | Incubation time (days) | Observed antifungal activity O (%) | Expected antifungal activity E (%) | Synergy factor O/E |
|---|---|---|---|---|
| Control | 4 | 0 | — | — |
| Natamycin 500 ppm | | 63 | — | — |
| Bixafen 2000 ppm | | 47 | — | — |
| Natamycin 500 ppm + bixafen 2000 ppm | | 93 | 80 | 1.2 |
| Control | 6 | 0 | — | — |
| Natamycin 500 ppm | | 28 | — | — |
| Bixafen 2000 ppm | | 32 | — | — |
| Natamycin 500 ppm + bixafen 2000 ppm | | 62 | 51 | 1.2 |
| Control | 9 | 0 | — | — |
| Natamycin 500 ppm | | 15 | — | — |
| Bixafen 2000 ppm | | 7 | — | — |
| Natamycin 500 ppm + bixafen 2000 ppm | | 29 | 21 | 1.4 |
| Control | 11 | 0 | — | — |
| Natamycin 500 ppm | | 13 | — | — |
| Bixafen 2000 ppm | | 9 | — | — |
| Natamycin 500 ppm + bixafen 2000 ppm | | 26 | 20 | 1.3 |
| Control | 14 | 0 | — | — |
| Natamycin 500 ppm | | 9 | — | — |
| Bixafen 2000 ppm | | 3 | — | — |
| Natamycin 500 ppm + bixafen 2000 ppm | | 19 | 12 | 1.6 |
| Control | 15 | 0 | — | — |
| Natamycin 500 ppm | | 5 | — | — |
| Bixafen 2000 ppm | | 0 | — | — |
| Natamycin 500 ppm + bixafen 2000 ppm | | 14 | 5 | 2.8 |

TABLE 9

Antifungal activity (%) of compositions comprising either 500 ppm natamycin, 1000 ppm bixafen or both on mandarins after incubation at 20° C.

| Antifungal composition | Incubation time (days) | Observed antifungal activity O (%) | Expected antifungal activity E (%) | Synergy factor O/E |
|---|---|---|---|---|
| Control | 4 | 0 | — | — |
| Natamycin 500 ppm | | 63 | — | — |

TABLE 9-continued

Antifungal activity (%) of compositions comprising either 500 ppm natamycin, 1000 ppm bixafen or both on mandarins after incubation at 20° C.

| Antifungal composition | Incubation time (days) | Observed antifungal activity O (%) | Expected antifungal activity E (%) | Synergy factor O/E |
|---|---|---|---|---|
| Bixafen 1000 ppm | | 37 | — | — |
| Natamycin 500 ppm + bixafen 1000 ppm | | 90 | 77 | 1.2 |
| Control | 6 | 0 | — | — |
| Natamycin 500 ppm | | 28 | — | — |
| Bixafen 1000 ppm | | 22 | — | — |
| Natamycin 500 ppm + bixafen 1000 ppm | | 58 | 44 | 1.3 |
| Control | 7 | 0 | — | — |
| Natamycin 500 ppm | | 16 | — | — |
| Bixafen 1000 ppm | | 6 | — | — |
| Natamycin 500 ppm + bixafen 1000 ppm | | 35 | 21 | 1.7 |
| Control | 9 | 0 | — | — |
| Natamycin 500 ppm | | 15 | — | — |
| Bixafen 1000 ppm | | 2 | — | — |
| Natamycin 500 ppm + bixafen 1000 ppm | | 24 | 17 | 1.4 |
| Control | 14 | 0 | — | — |
| Natamycin 500 ppm | | 9 | — | — |
| Bixafen 1000 ppm | | 0 | — | — |
| Natamycin 500 ppm + bixafen 1000 ppm | | 19 | 9 | 2.1 |
| Control | 15 | 0 | — | — |
| Natamycin 500 ppm | | 5 | — | — |
| Bixafen 1000 ppm | | 0 | — | — |
| Natamycin 500 ppm + bixafen 1000 ppm | | 15 | 5 | 3.0 |

TABLE 10

Antifungal activity (%) of compositions comprising either 250 ppm natamycin, 500 ppm bixafen or both on mandarins after incubation at 20° C.

| Antifungal composition | Incubation time (days) | Observed antifungal activity O (%) | Expected antifungal activity E (%) | Synergy factor O/E |
|---|---|---|---|---|
| Control | 4 | 0 | — | — |
| Natamycin 250 ppm | | 43 | — | — |
| Bixafen 500 ppm | | 40 | — | — |
| Natamycin 250 ppm + bixafen 500 ppm | | 80 | 66 | 1.2 |
| Control | 6 | 0 | — | — |
| Natamycin 250 ppm | | 18 | — | — |
| Bixafen 500 ppm | | 26 | — | — |
| Natamycin 250 ppm + bixafen 500 ppm | | 60 | 39 | 1.5 |
| Control | 7 | 0 | — | — |
| Natamycin 250 ppm | | 10 | — | — |
| Bixafen 500 ppm | | 10 | — | — |
| Natamycin 250 ppm + bixafen 500 ppm | | 44 | 19 | 2.3 |
| Control | 9 | 0 | — | — |
| Natamycin 250 ppm | | 8 | — | — |
| Bixafen 500 ppm | | 0 | — | — |
| Natamycin 250 ppm + bixafen 500 ppm | | 34 | 8 | 4.3 |
| Control | 11 | 0 | — | — |
| Natamycin 250 ppm | | 13 | — | — |
| Bixafen 500 ppm | | 0 | — | — |
| Natamycin 250 ppm + bixafen 500 ppm | | 29 | 13 | 2.2 |
| Control | 13 | 0 | — | — |
| Natamycin 250 ppm | | 12 | — | — |
| Bixafen 500 ppm | | 0 | — | — |

TABLE 10-continued

Antifungal activity (%) of compositions comprising either 250 ppm natamycin, 500 ppm bixafen or both on mandarins after incubation at 20° C.

| Antifungal composition | Incubation time (days) | Observed antifungal activity O (%) | Expected antifungal activity E (%) | Synergy factor O/E |
|---|---|---|---|---|
| Natamycin 250 ppm + bixafen 500 ppm | | 23 | 12 | 1.9 |
| Control | 15 | 0 | — | — |
| Natamycin 250 ppm | | 6 | — | — |
| Bixafen 500 ppm | | 0 | — | — |
| Natamycin 250 ppm + bixafen 500 ppm | | 15 | 6 | 2.5 |

TABLE 11

Antifungal activity (%) of compositions comprising either 250 ppm natamycin, 250 ppm bixafen or both on mandarins after incubation at 20° C.

| Antifungal composition | Incubation time (days) | Observed antifungal activity O (%) | Expected antifungal activity E (%) | Synergy factor O/E |
|---|---|---|---|---|
| Control | 3 | 0 | — | — |
| Natamycin 250 ppm | | 70 | — | — |
| Bixafen 250 ppm | | 65 | — | — |
| Natamycin 250 ppm + bixafen 250 ppm | | 100 | 90 | 1.1 |
| Control | 4 | 0 | — | — |
| Natamycin 250 ppm | | 43 | — | — |
| Bixafen 250 ppm | | 27 | — | — |
| Natamycin 250 ppm + bixafen 250 ppm | | 87 | 58 | 1.5 |
| Control | 6 | 0 | — | — |
| Natamycin 250 ppm | | 18 | — | — |
| Bixafen 250 ppm | | 28 | — | — |
| Natamycin 250 ppm + bixafen 250 ppm | | 56 | 41 | 1.4 |
| Control | 7 | 0 | — | — |
| Natamycin 250 ppm | | 10 | — | — |
| Bixafen 250 ppm | | 10 | — | — |
| Natamycin 250 ppm + bixafen 250 ppm | | 41 | 19 | 2.2 |
| Control | 9 | 0 | — | — |
| Natamycin 250 ppm | | 8 | — | — |
| Bixafen 250 ppm | | 0 | — | — |
| Natamycin 250 ppm + bixafen 250 ppm | | 26 | 8 | 3.3 |

TABLE 12

Number of moulded apples incubated at 20° C. after treatment with compositions comprising either 500 ppm natamycin, 2000 ppm bixafen or both.

| Antifungal composition | Number of moulded apples/total number of 10 apples during incubation time (in days) | | | |
|---|---|---|---|---|
| | Day 3-4 | Day 6 | Day 7 | Day 9-14 |
| Control | 10/10 | 10/10 | 10/10 | 10/10 |
| Natamycin 500 ppm | 9/10 | 10/10 | 10/10 | 10/10 |
| Bixafen 2000 ppm | 5/10 | 8/10 | 8/10 | 10/10 |
| Natamycin 500 ppm + bixafen 2000 ppm | 2/10 | 2/10 | 4/10 | 6/10 |

TABLE 13

Antifungal activity (%) of compositions comprising either 500 ppm natamycin, 2000 ppm bixafen or both on apples after incubation at 20° C.

| Antifungal composition | Incubation time (days) | Observed antifungal activity O (%) | Expected antifungal activity E (%) | Synergy factor O/E |
|---|---|---|---|---|
| Control | 3 | 0 | — | — |
| Natamycin 500 ppm | | 33 | — | — |
| Bixafen 2000 ppm | | 60 | — | — |
| Natamycin 500 ppm + bixafen 2000 ppm | | 87 | 73 | 1.2 |
| Control | 6 | 0 | — | — |
| Natamycin 500 ppm | | 6 | — | — |
| Bixafen 2000 ppm | | 39 | — | — |
| Natamycin 500 ppm + bixafen 2000 ppm | | 89 | 42 | 2.1 |
| Control | 9 | 0 | — | — |
| Natamycin 500 ppm | | 21 | — | — |
| Bixafen 2000 ppm | | 29 | — | — |
| Natamycin 500 ppm + bixafen 2000 ppm | | 75 | 44 | 1.7 |
| Control | 11 | 0 | — | — |
| Natamycin 500 ppm | | 26 | — | — |
| Bixafen 2000 ppm | | 30 | — | — |
| Natamycin 500 ppm + bixafen 2000 ppm | | 78 | 48 | 1.6 |
| Control | 14 | 0 | — | — |
| Natamycin 500 ppm | | 30 | — | — |
| Bixafen 2000 ppm | | 36 | — | — |
| Natamycin 500 ppm + bixafen 2000 ppm | | 85 | 56 | 1.5 |

TABLE 14

Number of moulded apples incubated at 20° C. after treatment with compositions comprising either 500 ppm natamycin, 1000 ppm bixafen or both.

| Antifungal composition | Day 3 | Day 4 | Day 6 | Day 7 | Day 9-14 |
|---|---|---|---|---|---|
| Control | 10/10 | 10/10 | 10/10 | 10/10 | 10/10 |
| Natamycin 500 ppm | 9/10 | 9/10 | 10/10 | 10/10 | 10/10 |
| Bixafen 1000 ppm | 6/10 | 6/10 | 8/10 | 9/10 | 10/10 |
| Natamycin 500 ppm + bixafen 1000 ppm | 2/10 | 3/10 | 4/10 | 5/10 | 6/10 |

TABLE 15

Antifungal activity (%) of compositions comprising either 500 ppm natamycin, 1000 ppm bixafen or both on apples after incubation at 20° C.

| Antifungal composition | Incubation time (days) | Observed antifungal activity O (%) | Expected antifungal activity E (%) | Synergy factor O/E |
|---|---|---|---|---|
| Control | 3 | 0 | — | — |
| Natamycin 500 ppm | | 33 | — | — |
| Bixafen 1000 ppm | | 47 | — | — |
| Natamycin 500 ppm + bixafen 1000 ppm | | 87 | 64 | 1.4 |
| Control | 6 | 0 | — | — |
| Natamycin 500 ppm | | 6 | — | — |
| Bixafen 1000 ppm | | 44 | — | — |
| Natamycin 500 ppm + bixafen 1000 ppm | | 78 | 48 | 1.6 |
| Control | 9 | 0 | — | — |
| Natamycin 500 ppm | | 21 | — | — |
| Bixafen 1000 ppm | | 38 | — | — |
| Natamycin 500 ppm + bixafen 1000 ppm | | 75 | 51 | 1.5 |
| Control | 11 | 0 | — | — |
| Natamycin 500 ppm | | 26 | — | — |
| Bixafen 1000 ppm | | 30 | — | — |
| Natamycin 500 ppm + bixafen 1000 ppm | | 74 | 48 | 1.5 |
| Control | 14 | 0 | — | — |
| Natamycin 500 ppm | | 30 | — | — |
| Bixafen 1000 ppm | | 21 | — | — |
| Natamycin 500 ppm + bixafen 1000 ppm | | 76 | 45 | 1.7 |

TABLE 16

Number of moulded apples incubated at 20° C. after treatment with compositions comprising either 250 ppm natamycin, 500 ppm bixafen or both.

| Antifungal composition | Day 6 | Day 7 | Day 9 |
|---|---|---|---|
| Control | 10/10 | 10/10 | 10/10 |
| Natamycin 250 ppm | 10/10 | 10/10 | 10/10 |
| Bixafen 500 ppm | 10/10 | 10/10 | 10/10 |
| Natamycin 250 ppm + bixafen 500 ppm | 5/10 | 6/10 | 8/10 |

TABLE 17

Antifungal activity (%) of compositions comprising either 250 ppm natamycin, 500 ppm bixafen or both on apples after incubation at 20° C.

| Antifungal composition | Incubation time (days) | Observed antifungal activity O (%) | Expected antifungal activity E (%) | Synergy factor O/E |
|---|---|---|---|---|
| Control | 6 | 0 | — | — |
| Natamycin 250 ppm | | 38 | — | — |
| Bixafen 500 ppm | | 33 | — | — |
| Natamycin 250 ppm + bixafen 500 ppm | | 72 | 59 | 1.2 |
| Control | 7 | 0 | — | — |
| Natamycin 250 ppm | | 42 | — | — |
| Bixafen 500 ppm | | 39 | — | — |
| Natamycin 250 ppm + bixafen 500 ppm | | 74 | 65 | 1.1 |
| Control | 9 | 0 | — | — |
| Natamycin 250 ppm | | 35 | — | — |
| Bixafen 500 ppm | | 17 | — | — |
| Natamycin 250 ppm + bixafen 500 ppm | | 58 | 46 | 1.3 |

TABLE 18

Number of moulded apples incubated at 20° C. after treatment with compositions comprising either 250 ppm natamycin, 250 ppm bixafen or both.

| | Number of moulded strawberries/ total number of 10 strawberries during incubation time (in days) | |
|---|---|---|
| Antifungal composition | Day 6-9 | Day 11-15 |
| Control | 10/10 | 10/10 |
| Natamycin 250 ppm | 10/10 | 10/10 |
| Bixafen 250 ppm | 10/10 | 10/10 |
| Natamycin 250 ppm + bixafen 250 ppm | 6/10 | 7/10 |

TABLE 19

Antifungal activity (%) of compositions comprising either 250 ppm natamycin, 250 ppm bixafen or both on apples after incubation at 20° C.

| Antifungal composition | Incubation time (days) | Observed antifungal activity O (%) | Expected antifungal activity E (%) | Synergy factor O/E |
|---|---|---|---|---|
| Control | 6 | 0 | — | — |
| Natamycin 250 ppm | | 38 | — | — |
| Bixafen 500 ppm | | 17 | — | — |
| Natamycin 250 ppm + bixafen 250 ppm | | 67 | 49 | 1.4 |
| Control | 9 | 0 | — | — |
| Natamycin 250 ppm | | 35 | — | — |
| Bixafen 500 ppm | | 13 | — | — |
| Natamycin 250 ppm + bixafen 250 ppm | | 75 | 43 | 1.7 |
| Control | 11 | 0 | — | — |
| Natamycin 250 ppm | | 42 | — | — |
| Bixafen 500 ppm | | 0 | — | — |
| Natamycin 250 ppm + bixafen 250 ppm | | 67 | 42 | 1.6 |
| Control | 14 | 0 | — | — |
| Natamycin 250 ppm | | 49 | — | — |
| Bixafen 500 ppm | | 6 | — | — |
| Natamycin 250 ppm + bixafen 250 ppm | | 73 | 53 | 1.4 |

TABLE 20

In vitro antifungal activity (%) of natamycin in combination with isopyrazam against *Botrytis cinerea* after incubation at 25° C.

| Antifungal composition | Incubation time (days) | Observed antifungal activity O (%) | Expected antifungal activity E (%) | Synergy factor O/E |
|---|---|---|---|---|
| Control | 3 | 0 | — | — |
| Natamycin 1.25 ppm | | 0 | — | — |
| Isopyrazam 6.25 ppm | | 0 | — | — |
| Natamycin 1.25 ppm + Isopyrazam 6.25 ppm | | 100 | 0 | >100 |

TABLE 21

In vitro antifungal activity (%) of natamycin in combination with isopyrazam or bixafen against *Penicillium italicum* after incubation at 25° C.

| Antifungal composition | Incubation time (days) | Observed antifungal activity O (%) | Expected antifungal activity E (%) | Synergy factor O/E |
|---|---|---|---|---|
| Control | 10 | 0 | — | — |
| Natamycin 0.63 ppm | | 0 | — | — |
| Natamycin 1.25 ppm | | 0 | | |
| Isopyrazam 25 ppm | | 50 | — | — |
| Bixafen 25 ppm | | 50 | — | — |
| Natamycin 0.63 ppm + Isopyrazam 25 ppm | | 75 | 50 | 1.5 |
| Natamycin 1.25 ppm + Bixafen 25 ppm | | 75 | 50 | 1.5 |

REFERENCES

Colby S R (1967), Calculating synergistic and antagonistic responses of herbicide combination. Weeds 15: 20-22.

Culbreath A K, Brenneman T B, Kemerait R C and Hammes G G (2008), Effect of the new pyrazole carboxamide fungicide penthiopyrad on late leaf spot and stem rot of peanut. Pest Manag. Sci. 65:66-73.

Lapeyre de Bellaire de L and Dubois C (1987), Distribution of Thiabendazole-Resistant *Colletotrichum musae* Isolates from Guadeloupe Banana Plantations. Plant disease 81:1378-1383.

Slinker B K (1998), The Statistics of Synergism. Journal of Mol. and Cell. Cardiology 30:723-731.

Vincentini C B, Romagnoli C, Andreotti E and Mares D (2007), Synthetic pyrazole derivatives as growth inhibitors of some phytopathogenic fungi. J. Agric. Food Chem. 55:10331-10338.

The invention claimed is:

1. A composition comprising natamycin and at least one antifungal compound from the family of pyrazole fungicides selected from the group consisting of bixafen and isopyrazam, wherein each of natamycin and at least one antifungal compound are present in synergistically effective amounts.

2. A composition according to claim 1, wherein the composition further comprises at least one additional compound selected from the group consisting of a sticking agent, a carrier, a colouring agent, a protective colloid, an adhesive, a herbicide, a fertilizer, a thickening agent, a sequestering agent, a thixotropic agent, a surfactant, a further antimicrobial compound, a detergent, a preservative, a spreading agent, a filler, a spray oil, a flow additive, a mineral substance, a solvent, a dispersant, an emulsifier, a wetting agent, a stabiliser, an antifoaming agent, a buffering agent, an UV-absorber and an antioxidant.

3. A composition according to claim 1, wherein the amount of natamycin is in a range from 0.005 g/l to about 100 g/l and the amount of the at least one antifungal compound from the family of pyrazole fungicides is in a range from about 0.0001 g/l to about 2000 g/l.

4. A kit comprising natamycin and at least one antifungal compound from the family of pyrazole fungicides selected from the group consisting of bixafen and isopyrazam, wherein natamycin and at least one antifungal compound are present in synergistically effective amounts.

5. A method for protecting a product against fungi by treating the product with a composition comprising natamycin and at least one antifungal compound from the family of pyrazole fungicides selected from the group consisting of bixafen and isopyrazam, wherein each of natamycin and at least one antifungal agent are present in synergistically effective amounts.

6. A method according to claim 5, wherein the product is treated with a composition that comprises natamycin and said at least one antifungal compound.

7. A method according to claim 5, wherein the product is at least one selected from the group consisting of a food product, a feed product, a pharmaceutical product, a cosmetic product and an agricultural product.

8. A method according to claim 7, wherein the product is an agricultural product.

9. A method according to claim 8, wherein the product is treated post-harvest.

10. A product comprising natamycin and at least one antifungal compound from the family of pyrazole fungicides selected from the group consisting of bixafen and isopyrazam, wherein each of natamycin and at least one antifungal compound are present in synergistically effective amounts.

11. A product according to claim 10, wherein the product is at least one selected from the group consisting of a food product, a feed product, a pharmaceutical product, a cosmetic product and an agricultural product.

12. A product according to claim 11, wherein the product is an agricultural product.

* * * * *